United States Patent [19]
Okamoto et al.

[11] Patent Number: 5,658,918
[45] Date of Patent: Aug. 19, 1997

[54] PURINE-2,8-DIONES AND PHARMACEUTICALLY ACCEPTABLE SALTS THEREOF

[75] Inventors: Kaoru Okamoto; Taisuke Hasegawa; Akio Namimatsu, all of Hyogo, Japan

[73] Assignee: Nippon Zoki Pharmaceutical Co., Ltd., Osaka, Japan

[21] Appl. No.: 409,054

[22] Filed: Mar. 23, 1995

[30] Foreign Application Priority Data

Mar. 25, 1994 [JP] Japan .................................. 6-079336

[51] Int. Cl.$^6$ ...................... A61K 31/52; C07D 473/28
[52] U.S. Cl. ............................. 514/262; 544/265
[58] Field of Search ................... 544/265; 514/262

[56] References Cited

FOREIGN PATENT DOCUMENTS

| | | |
|---|---|---|
| 52-120135 | 10/1977 | Japan . |
| 54-55733 | 5/1979 | Japan . |
| 60-58726 | 12/1985 | Japan . |
| 61-26527 | 6/1986 | Japan . |

OTHER PUBLICATIONS

Takino, Chem Abs 91, 129036 (1979).
Takino, Chem Abs 105, 91339 (1986).
Brown, Chem Abs 54, 5682d (1960).
Bergmann, JACS, 82, 598 (1960).

*Primary Examiner*—Mark L. Berch
*Attorney, Agent, or Firm*—Fisher, Christen & Sabol

[57] ABSTRACT

The present invention provides purine derivatives and pharmaceutically acceptable salts thereof which exhibit an inhibitory action towards nasal mucus secretion and are useful as pharmaceuticals for treatment of nasal secretion and rhinitis. The purine derivatives are represented by the following general formula:

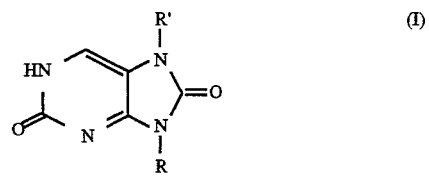

(I)

wherein R is alkyl or cycloalkyl, or optionally-substituted phenyl or phenylalkyl; R' is hydrogen or —COOX; and X is alkyl, alkenyl, alkoxyalkyl, phenyl or phenylalkyl. The compounds are useful as therapeutic and preventive agents for various types of rhinitis accompanied by acceleration of nasal mucus secretion and by the sneezing reflex such as allergic rhinitis. The compounds may be administered orally and exhibit low toxicity, little side effect and high safety. Accordingly, continuous long term administration of the pharmaceutical compositions may be performed for highly effective treatment of rhinitis.

24 Claims, No Drawings

PURINE-2,8-DIONES AND PHARMACEUTICALLY ACCEPTABLE SALTS THEREOF

FIELD OF THE INVENTION

The present invention relates to novel purine derivatives and pharmaceutically acceptable salts thereof having an inhibitory action towards nasal mucus secretion. The present invention also relates to pharmaceutical compositions which contain the derivatives and salts as an effective component.

BACKGROUND OF THE INVENTION

Allergy is a sensitive state of a living body owing to an antigen-antibody reaction. Allergies are classified into four types, type I to type IV, depending upon the reaction mechanism. Bronchial asthma, allergic rhinitis, urticaria, etc. which are representative allergic diseases from which many people suffer are due to a type I allergic reaction. A type I allergic reaction is an immediate type or an anaphylactic type reaction. In the type I allergic reaction, a degranulation takes place when antigen is bonded with IgE which is bonded with the cell surface of basophiles and mastocytes. Various allergic symptoms result when inflammatory mediators such as histamine and leucotriene are released.

For example, the allergic rhinitis from which increasing people suffer in recent years is classified into: 1) a whole-year allergy in which house dust is the main antigen, and 2) a seasonal allergy (pollinosis) primarily caused by pollen of Japanese cedar. The former starts when one is a baby or a small child and its symptoms continue. Accordingly, a continuous therapy is particularly necessary resulting in a demand for therapeutic and preventive agents which can be administered for long periods of time and which exhibit little side effect. In the case of rhinitis such as allergic rhinitis, it is an important therapy to remove unpleasant sensations caused by a promotion of secretion of nasal mucus. Therefore, an excellent agent for inhibiting the secretion of nasal mucus can be used as an effective therapeutic agent for rhinitis.

With respect to the pharmacological action of purine derivatives, Examined Japanese Patent Publications 58,726/85 and 26,527/86 disclose that 2,8-dihydroxypurine exhibits analgesic, sedative and antiallergic actions. Unfortunately this compound exhibits very poor solubility in both aqueous and nonaqueous solvents. For practical use as a drug, the compound has very little applicability.

The present inventors have found purine derivatives which are therapeutic agents for rhinitis which can be administered for long periods of time. The purine derivatives of the present invention exhibit an excellent action for inhibiting the secretion of nasal mucus. The compounds are more soluble in various solvents compared to the solubility of 2,8-dihydroxypurine. The present invention provides compounds which are readily soluble in aqueous solvents and which are readily absorbed into the bloodstream.

SUMMARY OF THE INVENTION

The present invention provides purine derivatives and pharmaceutically active salts thereof which exhibit significant inhibitory action towards the secretion of nasal mucus and are useful as drugs. The compounds of the present invention are effective as therapeutic and preventive agents towards various types of rhinitis which are accompanied by acceleration of nasal mucus secretion and by the sneezing reflex, such as allergic rhinitis. Compounds of the present invention may be administered orally and exhibit low toxicity, little side effect and high safety. Accordingly, continuous administration for extended periods of time is possible and they have a very high utility as pharmaceuticals for various types of rhinitis, such as allergic rhinitis, which require long term therapy.

The compounds of the present invention are represented by the following general formula (I):

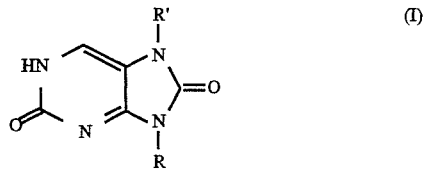

wherein R is alkyl or cycloalkyl, or optionally-substituted phenyl or phenylalkyl; R' is hydrogen or —COOX; and X is alkyl, alkenyl, alkoxyalkyl, phenyl or phenylalkyl. The compounds of the present invention also include pharmaceutically acceptable salts of the compounds represented by general formula I. The present invention also provides pharmaceutical compositions containing at least one of said compounds as an effective component. In preferred embodiments of the invention, the substituent at the 7-position, R', is —COOX. These compounds exhibit unexpectedly high absorption of the effective component into the blood by oral administration and low dosages for inhibiting nasal mucus secretion.

DETAILED DESCRIPTION OF THE INVENTION

The present invention relates to compounds represented by the following general formula (I) and pharmaceutically acceptable salts thereof and also to pharmaceutical compositions containing at least one of said compounds or salts as an effective component for the treatment of nasal mucus secretion and rhinitis:

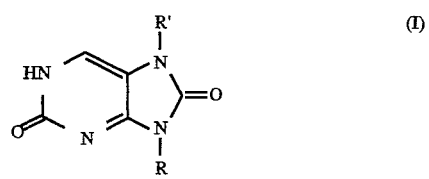

wherein R is alkyl or cycloalkyl, or optionally-substituted phenyl or phenylalkyl; R' is hydrogen or —COOX; and X is alkyl, alkenyl, alkoxyalkyl, phenyl or phenylalkyl.

Preferred examples of the alkyl represented by R or X in the above-mentioned general formula (I) are linear or branched $C_{1-20}$ alkyls such as methyl, ethyl, propyl, isopropyl, butyl, isobutyl, sec-butyl, tert-butyl, pentyl, isopentyl, neopentyl, tert-pentyl, hexyl, dimethylbutyl, heptyl, octyl, nonyl, decyl, undecyl, dodecyl, tridecyl, tetradecyl, pentadecyl, hexadecyl, heptadecyl, octadecyl, nonadecyl, icosyl, etc.

Preferred examples of the cycloalkyl represented by R are $C_{3-8}$ cycloalkyls such as cyclopropyl, cyclobutyl, cyclopentyl, cyclohexyl, cycloheptyl, cyclooctyl, etc.

Preferred examples of the phenylalkyl represented by R or X are those wherein a phenyl group is bonded with a linear or branched $C_{1-4}$ alkyl such as methyl, ethyl, propyl, isopropyl, butyl, isobutyl, sec-butyl, tert-butyl, etc. The phenyl or phenylalkyl represented by R may be substituted and examples of the substituent are alkyl (preferably a linear or branched $C_{1-4}$ alkyl such as methyl, ethyl, propyl, isopropyl, butyl, isobutyl, sec-butyl, tert-butyl, etc.), alkoxy (preferably a linear or branched $C_{1-4}$ alkoxy such as methoxy, ethoxy, propoxy, isopropoxy, butoxy, isobutoxy, sec-butoxy, tert-butoxy, etc.) and halogen such as fluorine, chlorine, bromine, iodine, etc.

Preferred examples of the alkenyl represented by X are linear or branched $C_{2-6}$ alkenyls such as ethenyl, 1-propenyl, 2-propenyl, 1-butenyl, 3-butenyl, sec-butenyl, pentenyl, isopentyl, 2-pentenyl, 3-pentenyl, 4-pentenyl, hexenyl, dimethylbutenyl, etc. Preferred examples of the alkoxyalkyl represented by X are linear or branched $C_{1-4}$ alkyls such as methyl, ethyl, propyl, isopropyl, butyl, isobutyl, sec-butyl, tert-butyl, etc. bonded with a linear or branched $C_{1-4}$ alkoxy such as methoxy, ethoxy, propoxy, isopropoxy, butoxy, isobutoxy, sec-butoxy, tert-butoxy, etc.

Preferred embodiments of the compounds of the present invention represented by the above-given general formula (I) having an action for inhibiting the secretion of nasal mucus are as follows. They are the preferred embodiments of the effective components of inhibiting agents for nasal mucus as well:

(1) Compounds of the present invention in which R' in the general formula (I) is hydrogen;

(2) Compounds of the present invention an which R is alkyl in the compounds given in the above paragraph (1);

(3) Compounds of the present invention in which R is isopropyl in the compounds given in the above paragraph (2);

(4) Compounds of the present invention in which R' in the general formula (I) is —COOX;

(5) Compounds of the present invention in which R is alkyl in the compounds given in the above paragraph (4);

(6) Compounds of the present invention an which R is ethyl in the compounds given in the above paragraph (5);

(7) Compounds of the present invention an which R is propyl in the compounds given in the above paragraph (5);

(8) Compounds of the present invention in which R is isopropyl in the compounds given in the above paragraph (5);

(9) Compounds of the present invention in which R is a linear or branched alkyl having four carbon atoms in the compounds given in the above paragraph (5);

(10) Compounds of the present invention in which X is alkyl in the compounds given in any of the above paragraphs (4) to (9);

(11) Compounds of the present invention in which X is a linear or branched alkyl having 1 to 6 carbon atoms in the compounds given in the above paragraph (10);

(12) Compounds of the present invention in which X is methyl in the compounds given in the above paragraph (10);

(13) Compounds of the present invention in which X is ethyl in the compounds given in the above paragraph (10);

(14) Compounds of the present invention in which X is propyl in the compounds given in the above paragraph (10);

(15) Compounds of the present invention in which X is isopropyl in the compounds given in the above paragraph (10);

(16) Compounds of the present invention in which X is a linear or branched alkyl having four carbon atoms in the compounds given in the above paragraph (10);

(17) Compounds of the present invention in which X is a linear or branched alkyl having five carbon atoms in the compounds given in the above paragraph (10); and

(18) Compounds of the present invention in which X is a linear or branched alkyl having six carbon atoms in the compounds given in the above paragraph (10).

The purine derivatives of the present invention include the pharmaceutically acceptable salts of the compounds represented by the above-mentioned general formula. Exemplary salts are salts of the compounds of general formula I with an alkali metal such as sodium and potassium, with an alkali earth metal such as calcium and magnesium and with a metal such as aluminum.

The purine derivatives of the present invention include metal complexes of the compounds of general formula I. Exemplary complexes of the present invention include complex compounds with zinc, nickel, cobalt, copper, iron, etc. Such salts or metal complexes may be manufactured by conventional methods starting from the purine derivatives of the present invention in the free state or by conversion from one salt or complex to another salt or complex.

When there are stereoisomers such as cis-trans isomers, optical isomers, conformational isomers, etc. in the compound of the present invention or when the compound of the present invention exists in a state of hydrates, the present invention includes all of such stereoisomers and hydrates.

The compounds of the present invention represented by the general formula (I) may, for example, be manufactured by the following methods:

(a) The compounds of the present invention in which the substituent R' is hydrogen may be manufactured by a catalytic reduction of 5-nitro-4-N-substituted cytosine having a substituent corresponding to the above-mentioned R with palladium-carbon or the like followed by melting the resulting 4,5-diamino compound with urea. Alternatively, they may be manufactured by the reaction of 5-amino-4-N-substituted cytosine with carbonyl diimidazole; and (b) The compounds of the present invention in which the substituent R' is —COOX may be manufactured by introducing a group —COOX into the 7-position of the compound obtained in the above method (a). For example, various esters of chloroformic acid (i.e. esters corresponding to X of the —COOX group) are made to react with the compound of the present invention in which the substituent R' is hydrogen whereupon the compounds of the present invention in which the substituent R' is —COOX may be manufactured.

The compounds of the present invention prepared as such may be purified by conventional means such as distillation and chromatography and may be identified by means of melting points, elementary analysis, IR, NMR, UV, mass spectrum, etc.

The present invention is illustrated by the following examples wherein all parts, percentages, and ratios are by weight and all temperatures are in ° C. unless indicated to the contrary:

EXAMPLE 1

4-N-Methyl-5-nitrocytosine (3.5 g) was subjected to a catalytic reduction in the presence of 0.7 g of 10% palladium-carbon in 400 ml of methanol to give a diamino compound. This compound was heated with 7.4 g of urea at 150° C. with stirring and the resulting brown solid was dissolved in a 1N sodium hydroxide solution followed by treating with active carbon. This mixture was neutralized with acetic acid and the crystals separated out therefrom were filtered and washed with water. The same treatment with active carbon was repeated several times to purify the crystals whereupon 1.6 g of 9-methyl-1,2,7,8-tetrahydro-9H-purine-2,8-dione (compound 1) were obtained. The melting point and elementary analysis for the compound were:

Melting point was not lower than 320° C. Elementary analysis calculated for $C_6H_6N_4O_2$: Calcd: C=43.38%, H=3.64%, N=33.72% Found: C=43.23%, H=3.74%, N=33.69%.

Compounds 2 through 11 were prepared in a manner similar to the preparation of Compound 1. Compounds 2 through 11 and their melting points and elementary analyses are:

9-Ethyl-1,2,7,8-tetrahydro-9H-purine-2,8-dione (Compound 2).

Melting point was not lower than 320° C. MS (m/z): 180 ($M^+$). Elementary analysis calculated for $C_7H_8N_4O_2$: Calcd: C=46.67%, H=4.48%, N=31.10% Found: C=46.87%, H=4.65%, N=31.12%.

9-Isopropyl-1,2,7,8-tetrahydro-9H-purine-2,8-dione (Compound 3).

Melting point was not lower than 320° C. MS (m/z): 194 ($M^+$). Elementary analysis calculated for $C_8H_{10}N_4O_2$: Calcd: C=49.48%, H=5.19%, N=28.58% Found: C=49.79%, H=5.36%, N=29.10%.

9-Butyl-1,2,7,8-tetrahydro-9H-purine-2,8-dione (Compound 4).

Melting point was not lower than 320° C. MS (m/z): 208 ($M^+$). Elementary analysis calculated for $C_9H_{12}N_4O_2$: Calcd: C=51.92%, H=5.81%, N=26.91% Found: C=52.10%, H=5.87%, N=26.98%.

9-(1,3-Dimethylbutyl)-1,2,7,8-tetrahydro-9H-purine-2,8-dione (Compound 5).

Melting point was not lower than 320° C. MS (m/s): 236 ($M^+$). Elementary analysis calculated for $C_{11}H_{16}N_4O_2 \cdot 0.2H_2O$: Calcd: C=55.09%, H=6.89%, N=23.36% Found: C=55.27%, H=6.92%, N=23.07%.

9-Cyclohexyl-1,2,7,8-tetrahydro-9H-Purine-2,8-dione (Compound 6).

Melting point was not lower than 320° C. MS (m/s): 234 ($M^+$). Elementary analysis calculated for $C_{11}H_{14}N_4O_2$: Calcd: C=56.40%, H=6.02%, N=23.92% Found: C=56.59%, H=6.05%, N=24.00%.

9-Phenyl-1,2,7,8-tetrahydro-9H-purine-2,8-dione (Compound 7).

Melting point was not lower than 320° C. Elementary analysis calculated for $C_{11}H_8N_4O_2 \cdot 0.1AcOH \cdot 0.4H_2O$: Calcd: C=55.72%, H=3.84%, N=23.20% Found: C=55.87%, H=3.68%, N=23.14%.

9-Benzyl-1,2,7,8-tetrahydro-9H-purine-2,8-dione (Compound 8).

Melting point was not lower than 320° C. Elementary analysis calculated for $C_{12}H_{10}N_4O_2$: Calcd: C=59.50%, H=4.16%, N=23.13% Found: C=59.83%, H=4.10%, N=23.45%.

9-(2-Phenylethyl)-1,2,7,8-tetrahydro-9H-purine-2,8-dione (Compound 9).

Melting point was not lower than 320° C. Elementary analysis calculated for $C_{13}H_{12}N_4O_2$: Calcd: C=60.93%, H=4.72%, N=21.86% Found: C=61.07%, H=4.87%, N=22.12%.

9-(4-Methoxyphenyl)-1,2,7,8-tetrahydro-9H-purine-2,8-dione (Compound 10).

Melting point was not lower than 320° C. Elementary analysis calculated for $C_{12}H_{10}N_4O_3 \cdot 0.1AcOH \cdot 0.4H_2O$ Calcd: C=53.98%, H=4.16%, N=20.64% Found: C=53.92%, H=3.97%, N=20.77%.

9-(2-Fluorobenzyl)-1,2,7,8-tetrahydro-9H-purine-2,8-dione (Compound 11).

Melting point was not lower than 320° C. Elementary analysis calculated for $C_{12}H_9FN_4O_2$: Calcd: C=55.39%, H=3.49%, N=21.53% Found: C=55.33%, H=3.36%, N=21.37%.

EXAMPLE 2

5-Amino-4-N-isopropylcytosine (21 g) was suspended in 200 ml of dimethylformamide and 22.3 g of carbonyldiimidazole were added thereto at room temperature. After five minutes, the reaction mixture became transparent. This mixture was stirred for 30 minutes and 400 ml of ether were added thereto. The crystals which were separated out therefrom were filtered, washed with ether and dried to give 20.7 g of the compound 3 of the present invention.

EXAMPLE 3

The compound 3 (350 mg) was suspended in a mixed solvent comprising dry dimethylformamide and dry dimethyl sulfoxide and 76 mg of sodium hydride were added thereto at 0° C. in an atmosphere of argon. The mixture was stirred for 10 minutes, 0.15 ml of methyl chloroformate was dropped thereinto at 0° C. and the mixture was stirred at room temperature for 30 minutes. A saturated aqueous solution of ammonium chloride was added, the mixture was diluted with water and extracted with chloroform three times. The extracted chloroform layer was washed with water and a saturated sodium chloride solution, dried over sodium sulfate and the solvent was evaporated therefrom in vacuo. The resulting crude crystals were recrystallized from ether-chloroform to give 141 mg of 9-isopropyl-7-methoxycarbonyl-1,2,7,8-tetrahydro-9H-purine-2,8-dione (Compound 12) as white crystals. The melting point and elemental analysis of the compound are:

Melting point: 303°–306° C. MS (m/z): 252 ($M^+$). Elementary analysis calculated for $C_{10}H_{12}N_4O_4$: Calcd: C=47.62%, H=4.80%, N=22.21% Found: C=47.65%, H=4.83%, N=22.18%.

Compounds 13 through 25 were prepared in a manner similar to the preparation of Compound 12. Compounds 13 through 25 and their melting points and elementary analyses are:

7-Ethoxycarbonyl-9-isopropyl-1,2,7,8-tetrahydro-9H-purine-2,8-dione (Compound 13).

Melting point: 200°–202° C. MS (m/z): 266 ($M^+$). Elementary analysis calculated for $C_{11}H_{14}N_4O_4$: Calcd: C=49.63%, H=5.30%, N=21.04% Found: C=49.57%, H=5.31%, N=20.95%.

9-Isopropyl-7-propoxycarbonyl-1,2,7,8-tetrahydro-9H-purine-2,8-dione (Compound 14).

Melting point: 206°–208° C. MS (m/z): 280 ($M^+$). Elementary analysis calculated for $C_{12}H_{16}N_4O_4$: Calcd: C=51.42%, H=5.75%, N=19.99% Found: C=51.12%, H=5.72%, N=19.94%.

9-Isopropyl-7-isopropoxycarbonyl-1,2,7,8-tetrahydro-9H-purine-2,8-dione (Compound 15).

Melting point: 216°–218° C. MS (m/z): 280 ($M^+$). Elementary analysis calculated for $C_{12}H_{16}N_4O_4 \cdot 0.4H_2O$: Calcd: C=50.13%, H=5.89%, N=19.49% Found: C=50.29%, H=5.61%, N=19.47%.

7-Allylcarbonyl-9-isopropyl-1,2,7,8-tetrahydro-9H-purine- 2,8-dione (Compound 16). Melting point: 201°–203° C. MS (m/z): 278 ($M^+$). Elementary analysis calculated for $C_{12}H_{14}N_4O_4$: Calcd: C=51.80%, H=5.07%, N=20.14% Found: C=51.46%, H=5.10%, N=19.84%.

7-Butoxycarbonyl-9-isopropyl-1,2,7,8-tetrahydro-9H-purine-2,8-dione (Compound 17).

Melting point: 217°–219° C. MS (m/z): 294 ($M^+$). Elementary analysis calculated for $C_{13}H_{18}N_4O_4$: Calcd: C=53.05%, H=6.16%, N=19.04% Found: C=53.00%, H=6.14%, N=19.00%.

7-Isobutoxycarbonyl-9-isopropyl-1,2,7,8-tetrahydro-9H-purine-2,8-dione (Compound 18).

Melting point: 217°–219° C. MS (m/z): 294 (M$^+$). Elementary analysis calculated for $C_{13}H_{18}N_4O_4$: Calcd: C=53.05%, H=6.16%, N=19.04% Found: C=53.06%, H=6.14%, N=18.96%.

7-Hexyloxycarbonyl-9-isopropyl-1,2,7,8-tetrahydro-9H-purine-2,8-dione (Compound 19).

Melting point: 189°–191° C. MS (m/z): 322 (M$^+$). Elementary analysis calculated for $C_{15}H_{22}N_4O_4$: Calcd: C=55.89%, H=6.88%, N=17.38% Found: C=55.94%, H=6.84%, N=17.41%.

9-Isopropyl-7-octyloxycarbonyl-1,2,7,8-tetrahydro-9H-purine-2,8-dione (Compound 20). Melting point: 185°–187° C. MS (m/z): 350 (M$^+$). Elementary analysis calculated for $C_{17}H_{26}N_4O_4$: Calcd: C=58.27%, H=7.48%, N=15.99% Found: C=58.19%, H=7.40%, N=16.02%.

7-(2-Ethylhexyloxycarbonyl)-9-isopropyl-1,2,7,8-tetrahydro-H-purine-2,8-dione (Compound 21).

Melting point: (oily substance). MS (m/z): 350 (M$^+$). Elementary analysis calculated for $C_{17}H_{26}N_4O_4$: Calcd: C=58.27%, H=7.48%, N=15.99% Found: C=58.20%, H=7.54%, N=16.02%.

7-Hexadecyloxycarbonyl-9-isopropyl-1,2,7,8-tetrahydro-9H-purine-2,8-dione (Compound 22).

Melting point: 141°–143° C. MS (m/z): 462 (M$^+$). Elementary analysis calculated for $C_{25}H_{42}N_4O_4$: Calcd: C=64.90%, H=9.15%, N=12.11% Found: C=64.78%, H=9.18%, N=12.01%.

9-Isopropyl-7-(2-methoxyethoxycarbonyl)-1,2,7,8-tetrahydro-H-purine-2,8-dione (Compound 23).

Melting point: 218°–220° C. MS (m/z): 296 (M$^+$). Elementary analysis calculated for $C_{12}H_{16}N_4O_5$: Calcd: C=48.64%, H=5.44%, N=18.91% Found: C=48.64%, H=5.47%, N=18.90%.

9-Isopropyl-7-phenoxycarbonyl-1,2,7,8-tetrahydro-9H-purine-2,8-dione (Compound 24).

Melting point: 255°–257° C. MS (m/z): 314 (M$^+$). Elementary analysis calculated for $C_{15}H_{14}N_4O_4 \cdot 0.5H_2O$: Calcd: C=55.73%, H=4.68%, N=17.33% Found: C=55.32%, H=4.55%, N=17.21%.

7-Benzyloxycarbonyl-9-isopropyl-1,2,7,8-tetrahydro-9H-purine-2,8-dione (Compound 25).

Melting point: 210°–212° C. Elementary analysis calculated for $C_{16}H_{16}N_4O_4$: Calcd: C=58.53%, H=4.91%, N=17.06% Found: C=58.21%, H=4.96%, N=16.86%.

EXAMPLE 4

The compound 2, 4 or 9 was used as a starting material and treated with ethyl chloroformate in the same manner as in Example 3 to give the following compounds 26, 27, and 28, respectively:

7-Ethoxycarbonyl-9-ethyl-1,2,7,8-tetrahydro-9H-purine-2,8-dione (Compound 26).

Melting point: 220°–223° C. MS (m/z): 252 (M$^+$). Elementary analysis calculated for $C_{10}H_{12}N_4O_4 \cdot 0.1H_2O$: Calcd: C=47.28%, H=4.84%, N=22.06% Found: C=47.44%, H=4.73%, N=21.86%.

9-Butyl-7-Ethoxycarbonyl-1,2,7,8-tetrahydro-9H-purine-2,8-dione (Compound 27).

Melting point: 209°–211° C. MS (m/z): 280 (M$^+$). Elementary analysis calculated for $C_{12}H_{16}N_4O_4$: Calcd: C=51.42%, H=5.75%, N=19.99% Found: C=51.33%, H=5.75%, N=19.88%.

7-Ethoxycarbonyl-9-(2-phenylethyl)-1,2,7,8-tetrahydro-9H-purine-2,8-dione (Compound 28).

Melting point: 235°–237° C. MS (m/z): 328 (M$^+$). Elementary analysis calculated for $C_{16}H_{16}N_4O_4 \cdot 0.2H_2O$: Calcd: C=57.90%, H=4.98%, N=16.88% Found: C=58.01%, H=4.96%, N=16.89%.

EXAMPLE 5

Compounds of the present invention were evaluated for inhibitory action towards nasal mucus secretion by preparing guinea pigs having sensitized nasal mucus membranes, measuring rate of inhibition of nasal mucus secretion, and measuring absorption into blood:

1) Preparation of guinea pigs sensitive to nasal mucous membrane by an active sensitization with egg ovalbumin.

Ovalbumin (1 microgram; dissolved in 1 ml of a physiological saline solution) was intraperitoneally administered for 6 to 7 times on a biweekly basis to guinea pigs using 5 mg of aluminum hydride gel as an adjuvant. After two weeks from the final sensitization, 50 microliter of a 1% ovalbumin solution were nasally administered into both nostrils for not less than 5 times every 3 to 7 days to prepare guinea pigs which were sensitive to nasal mucous membrane.

2) Inhibitory action towards the secretion of nasal mucus induced by antigen.

Ovalbumin (0.25 mg) was dropped into one of the nostrils to induce a nasal allergic disease and an evaluation of the pharmaceutical effect was carried out using the amount of nasal mucus secretion which was induced in another nostril as an index. The compound to be tested was orally administered (1 mg/kg) at 60 minutes before the nasal disease was induced and the secreted amount of the nasal mucus was measured according to a method by Namimatsu, et al [Int. Arch. Allergy Immunol., vol. 95, pages 29–34 (1991)] using a dyed nasal mucus string whereupon the inhibitory action of the test compound to the secretion of nasal mucus was determined.

An example of the results on the inhibitory action towards the nasal mucus secretion by the compounds of the present invention is given in Table 1:

TABLE 1

| Compound Tested | Inhibiting Rate to Nasal Mucus Secretion |
|---|---|
| Compound 2 | 14.2% |
| Compound 3 | 39.6% |
| Compound 4 | 15.6% |
| Compound 6 | 13.3% |
| Compound 8 | 15.4% |
| Compound 11 | 13.2% |

3) Improvement in absorption into blood

It is apparent from the test result given in the above Table 1 that the compounds of the present invention of the general formula (I) in which the substituent R' is hydrogen exhibit an inhibitory action to the secretion of nasal mucus by oral administration. Although those compounds have an improved solubility in various kinds of solvents as compared to the solubility of 2,8-dihydroxypurine, they are still unable to be easily dissolved in aqueous solvents whereby their absorption into blood is low.

In view of the above, an improvement was carried out by introducing a —COOX group into the 7-position of those compounds for increasing their solubility in aqueous solvents such as water and for elevating their absorption into blood. As a result, it has been found that, after being absorbed into blood, the —COOX group introduced into the 7-position was detached and decomposed as a result of hydrolysis, etc. by an esterase existing in the blood whereupon the administered compound was converted to a pharmaceutically effective compound in which the substituent R' was hydrogen. Thus, introduction of the substituent —COOX into the 7-position made it possible to facilitate solubilization and the absorption into blood of the compounds of the present invention. As shown hereinafter, the compounds of the present invention in which R' is —COOX exhibit an unexpectedly superior absorption of the effective component into blood by oral administration whereupon the above-mentioned nasal mucus inhibitory action is achieved in lower concentrations than in the case of the compounds where R' is hydrogen.

An example of the results of the investigation of absorption of the compounds of the present invention having a substituent —COOX at the 7-position into blood by oral administration is:

A compound of the present invention was orally administered to a guinea pig in an amount of 51.5 micromoles/kg and the absorption rate of the compound into blood was given using the blood level of the compound where the substituent at the 7-position was detached (identical with the compound 3) as an index. The results for several compounds are presented in Table 2:

TABLE 2

| Compound | Blood Level of the Compound 3(microgram/ml) after | | | |
|---|---|---|---|---|
| | 15 min | 30 min | 1 hr | 2 hr |
| 3 (Control) | 0.02 | 0.03 | 0.14 | 0.27 |
| 12 | 0.91 | 1.08 | 0.79 | 0.35 |
| 13 | 3.59 | 2.27 | 1.17 | 0.28 |
| 14 | 2.42 | 2.57 | 1.57 | 0.51 |
| 15 | 6.43 | 5.52 | 2.85 | 0.59 |
| 16 | 0.57 | 0.71 | 1.30 | 0.39 |
| 17 | 4.31 | 3.54 | 1.79 | 0.50 |
| 18 | 4.71 | 3.55 | 1.47 | 0.62 |
| 19 | 1.05 | 1.25 | 0.71 | 0.38 |
| 21 | 1.12 | 0.94 | 0.80 | 0.51 |
| 24 | 0.59 | 0.72 | 1.01 | 0.31 |
| 25 | 0.60 | 0.85 | 0.90 | 0.32 |

As shown in Table 1, the compounds of the present invention exhibit a significant inhibitory action towards nasal mucus secretion induced by antigen in the guinea pigs sensitive to nasal mucous membrane by an active sensitization with ovalbumin. It is also apparent from the results of Table 2 that, in the case of the compounds of the present invention where the substituent at the 7-position is —COOX, absorption of the effective component into blood by oral administration was significantly improved. In addition, an improvement was noted with respect to the dose for achieving the action of inhibiting nasal mucus secretion. Further, the compounds of the present invention showed an excellent inhibitory action towards a sneezing reflex when the guinea pig sensitive to nasal mucous membrane was subjected to an antigenic stimulation. Consequently, the compounds of the present invention are effective as therapeutic and preventive agents for various types of rhinitis accompanied by acceleration of nasal mucus secretion and by the sneezing reflex, such as allergic rhinitis. Moreover, the compounds of the present invention can be administered orally and exhibit low toxicity, little side effect and high safety. Accordingly, long term continuous administration is possible. The compounds of the present invention have a very high utility as drugs for various types of rhinitis, such as allergic rhinitis, which require prolonged therapy.

The compounds of the present invention can be made into pharmaceutical preparations by combining one or more of the compounds with at least one suitable pharmaceutical carrier or diluent. Any of the known methods for providing preparations, such as for oral administrations (e.g. tablets, capsules, powders, liquids, etc.) and for parenteral administrations (e.g. for subcutaneous, intravenous, intramuscular, intrarectal and intranasal administrations) may be used to produce the pharmaceutical compositions of the present invention. Alternatively, fine particles of the compound of the present invention may be administered to mucous membranes such as those of the nose, throat and trachea in the form of a liquid for spraying, a dry powder or a liquid aerosol.

In the prescription or formulation, the compounds of the present invention may be used as pharmaceutically acceptable salts thereof. The compounds of the present invention and their salts may be used either solely or jointly in pharmaceutically effective amounts for treating animals or humans. They may also be used in pharmaceutically effective amounts in combination with pharmaceutically effective amounts of other pharmaceutically active components.

In the case of preparations for oral administration, the compounds of the present invention and their salts may be made into tablets, diluted powders, granules or capsules either alone or together with one or more suitable additives. Exemplary of additives which may be used are conventional fillers (e.g. lactose, sugar, glucose, mannitol, corn starch, potato starch, etc.) as well as binders (e.g. crystalline cellulose, cellulose derivatives, gum arabicum, tragacanth solution, sodium alginate solution, gelatin, etc.), disintegrating agents (e.g. corn starch, potato starch, carboxymethyl cellulose, etc.), lubricants (e.g. talc, magnesium stearate, etc.), bulking agents, moisturizing agents, buffers, preservatives, perfumes, and the like.

It is also possible to prepare pharmaceutical preparations other than the above-mentioned ones such as suppositories, cataplasms, ointments, etc. which are most suitable for therapy depending upon the state of the patient and the type of the disease.

The preferred dosage of the compound of the present invention varies depending upon the subject to be administered (age, body weight, symptom, etc. of the patient), dosage form, route of administration, term for administration, etc. To achieve the desired result, the compound may be usually administered by the oral route with a daily dose of 0.02–200 mg, preferably 0.1–100 mg, to common adults either once daily or several times a day.

In the case of parenteral administration using injections for example, the preferred dosage will be from one-third to one-tenth of the above-mentioned oral dosage because of the effects of absorption, etc. in the oral route.

In the case of local administration such as by an intranasal route, an amount of 0.01–50 mg of the effective component may be locally administered into the nostrils several times a day to achieve a desired effect.

An example of a pharmaceutical preparation in tablet form using the compounds of the present invention as an effective component is given in Table 3:

TABLE 3

| Tablet Formulations | |
|---|---|
| Components | Amount per Tablet |
| Compound of the Present Invention | 1 mg |
| Lactose | 150 mg |
| Corn starch | 40 mg |
| Magnesium stearate | 10 mg |
| Total | 201 mg |

What is claimed is:

1. A compound which is represented by the following formula (I) or a pharmaceutically acceptable salt thereof:

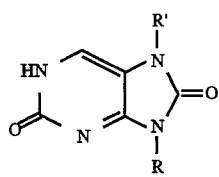
(I)

wherein R is alkyl, cycloalkyl, phenyl which may be substituted with alkoxy or halogen, or phenylalkyl which may be substituted with alkyl, alkoxy, or halogen; R' is hydrogen or —COOX; and X is alkyl, alkenyl, alkoxyalkyl, phenyl or phenylalkyl, with the proviso that formula (I) does not represent 9-methyl-1,2,7,8-tetrahydro-9H-purine-2,8-dione or a pharmaceutically acceptable salt of 9-methyl-1,2,7,8-tetrahydro-9H-purine-2,8- dione.

2. A compound as claimed in claim 1 wherein R' is hydrogen.

3. A compound as claimed in claim 2 wherein R is alkyl.

4. A compound as claimed in claim 3 wherein R is isopropyl.

5. A compound as claimed in claim 1 wherein R' is —COOX.

6. A compound as claimed in claim 5 wherein R is alkyl.

7. A compound as claimed in claim 6 wherein R is a linear or branched alkyl having 1 to 4 carbon atoms.

8. A compound as claimed in claim 7 wherein R is isopropyl.

9. A compound as claimed in claim 5 wherein X is alkyl.

10. A compound as claimed in claim 9 wherein X is a linear or branched alkyl having 1 to 6 carbon atoms.

11. A compound as claimed in claim 9 wherein R is alkyl.

12. A compound as claimed in claim 11 wherein R is a linear or branched alkyl having 1 to 4 carbon atoms.

13. A compound as claimed in claim 12 wherein R is isopropyl.

14. A compound as claimed in claim 1 which is a pharmaceutically acceptable salt of a compound of formula (I).

15. A pharmaceutical composition comprising a pharmaceutically effective mount of at least one compound represented by the following formula (I) or a pharmaceutically acceptable salt thereof as an effective component:

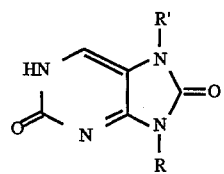
(I)

wherein R is alkyl, cycloalkyl, phenyl which may be substituted with alkoxy or halogen, or phenylalkyl which may be substituted with alkyl, alkoxy, or halogen; R' is hydrogen or —COOX; and X is alkyl, alkenyl, alkoxyalkyl, phenyl or phenylalkyl, and a pharmaceutically acceptable carrier or pharmaceutically acceptable diluent.

16. A pharmaceutical composition as claimed in claim 15 wherein R' is hydrogen and R is alkyl.

17. A pharmaceutical composition as claimed in claim 15 wherein R' is —COOX and R is alkyl.

18. A pharmaceutical composition as claimed in claim 17 wherein X is alkyl.

19. A pharmaceutical composition as claimed in claim 18 wherein R is a linear or branched alkyl having 1 to 4 carbon atoms.

20. A pharmaceutical composition as claimed in claim 19 wherein R is isopropyl.

21. A pharmaceutical composition as claimed in claim 15 comprising a pharmaceutically acceptable salt of a compound of formula (I).

22. A method for inhibiting nasal mucus secretion comprising administering a pharmaceutically effective amount of a compound which is represented by the following formula (I) or a pharmaceutically acceptable salt thereof:

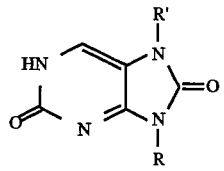
(I)

wherein R is alkyl, cycloalkyl, phenyl which may be substituted with alkoxy or halogen, or phenylalkyl which may be substituted with alkyl, alkoxy or halogen; R' is hydrogen or —COOX; and X is alkyl alkenyl, alkoxyalkyl, phenyl or phenylalkyl.

23. A compound as claimed in claim 3 wherein R is selected from the group consisting of ethyl, propyl, isopropyl, butyl, isobutyl, sec-butyl tert-butyl, pentyl, isopentyl, neopentyl, tert-pentyl, hexyl, dimethylbutyl, heptyl, octyl, nonyl, decyl, undecyl, dodecyl, tridecyl, tetradecyl, pentadecyl, hexadecyl, heptadecyl, octadecyl, nonadecyl, and icosyl.

24. A compound as claimed in claim 3 wherein R is selected from the group consisting of ethyl, isopropyl, and butyl.

* * * * *